United States Patent
Gibbons

[11] Patent Number: 5,980,475
[45] Date of Patent: Nov. 9, 1999

[54] ORTHOPEDIC PROTECTION DEVICE

[76] Inventor: Patrick J. Gibbons, 2702 4th St., Altoona, Pa. 16601

[21] Appl. No.: 08/511,757

[22] Filed: Aug. 7, 1995

[51] Int. Cl.$^6$ ........................................................ A61F 5/00
[52] U.S. Cl. ................................. 602/11; 602/23; 602/30
[58] Field of Search ................................ 602/3, 5, 11–14, 602/23, 30, 60, 62, 63, 65; 128/882; 623/29, 33, 36, 53; 2/239, DIG. 3; 36/110, 93, 29, 71, 72 R, 77 R, 77 M

[56] References Cited

U.S. PATENT DOCUMENTS

| | | |
|---|---|---|
| D. 291,621 | 9/1987 | Herman . |
| 2,703,405 | 3/1955 | Smallberg, Sr. ........................... 602/3 |
| 3,263,679 | 8/1966 | Hass ..................................... 602/11 X |
| 3,487,830 | 1/1970 | Pruett .................................... 2/239 |
| 3,773,041 | 11/1973 | Bogar . |
| 3,802,424 | 4/1974 | Newell ..................................... 602/3 |
| 4,061,138 | 12/1977 | Bernstein . |
| 4,103,438 | 8/1978 | Fron . |
| 4,454,872 | 6/1984 | Brouhard . |
| 4,759,353 | 7/1988 | Melendez et al. ........................... 602/4 |
| 4,911,151 | 3/1990 | Rankin et al. .............................. 602/3 |
| 5,014,448 | 5/1991 | Perrone ................................. 602/23 X |
| 5,257,969 | 11/1993 | Mance .................................. 602/30 X |
| 5,437,621 | 8/1995 | Andrews et al. ..................... 602/62 X |
| 5,452,527 | 9/1995 | Gaylard ................................. 602/23 X |

Primary Examiner—Danton D. DeMille
Assistant Examiner—Denise Pothier
Attorney, Agent, or Firm—Charles N. Quinn, Esq.

[57] ABSTRACT

An orthopedic protective device to protect limb extremities against injury. The device is typically used in conjunction with a cast, and encloses the limb extremity, while providing airflow within the device to reduce the risk of infection. A combination of gripping strips and gripping straps provide an easy means to attach and remove the device from the extremity. The device can also be used in combination with a surgical boot to protect the device and the cast from damage that may occur when the patient walks.

17 Claims, 5 Drawing Sheets

ORTHOPEDIC PROTECTION DEVICE

FIELD OF INVENTION

This invention relates to methods and apparatus for orthopedic protection, and more specifically to methods and apparatus for to protecting a limb extremity by enclosing the generally exposed limb extremity.

DISCUSSION OF PRIOR ART

Following surgery or other trauma to an extremity such as a hand or foot, an orthopedic protection device is frequently used in conjunction with a cast. The orthopedic protection device protects the portion of the extremity that is not enclosed by the cast. These devices meet the unique needs of orthopedic patients such as the need for the device to operate in conjunction with a cast, and the need for the device to protect the extremity without contacting the end of the extremity.

Although orthopedic protection devices are generally known, the known devices suffer from one of several shortcomings. The known devices either fail to fully protect the limb extremity, are permanently connected to the cast, cannot fit within a surgical boot, or depend upon a special cast.

For example, U.S. Pat. No. 3,773,041 to Bogar and U.S. Pat. No. 4,061,138 to Bernstein disclose toe protectors that require a special cast. The device in Bogar depends upon a special elongated walking tip built into the cast. The device attaches to the walking tip so that without a walking tip the device cannot be used.

The protective device disclosed in Bernstein must be molded directly into the cast. Not only does this complicate layup of the cast, but it increases the risk of infection by making it impossible to remove the device without removing the cast. As can be seen, these two devices unnecessarily complicate both the design of the cast and the method of using the protective device.

Brouhard U.S. Pat. No. 4,454,872 and Bogar disclose devices that do not completely protect the injured extremity. Neither device completely encloses the extremity to protect it from all angles. The device in Brouhard only provides a protective strip extending vertically around the periphery of the extremity; it fails to protect both the top and the bottom of the extremity. Similarly, the device in Bogar provides the same limited protection with the addition of a single narrow bar extending under the bottom of the extremity. Without complete enclosure, the extremity is subject to a variety of forces that can damage it and extend the recuperation period.

Because surgical boots are commonly used with a foot cast, it is desirable to have a protector that can easily be accommodated within a surgical boot. However, devices with curved or irregularly shaped bottoms, such as those disclosed by Brouhard and Bogar, create difficulties when used in conjunction with a surgical boot.

Other foot protectors, such as those disclosed in From U.S. Pat. No. 4,103,438 and Herman U.S. Pat. No. Des. 291,621, fail to meet the unique need of orthopedic patients. Herman discloses an ornamental protector fitting over a shoe, while From discloses a plastic insert placed into a clog to provide impact resistance. Because patients with casts cannot wear either a shoe or a clog on an injured foot, neither From nor Herman meet the needs of orthopedic patients.

SUMMARY OF THE INVENTION

This invention provides methods and apparatus for protecting a limb extremity. The apparatus includes an open-ended bubble, means for securing the bubble onto a limb extremity, a conventional surgical boot, and means for securing the bubble within the surgical boot.

The bubble has an opening on one end so that a limb extremity can be placed within the bubble. Preferably, the bubble is of single piece construction made from a transparent plastic. The bubble preferably has a top, a bottom, two sides and a curved front. The bottom is preferably generally planar and extends longitudinally from the open end. Preferably, the end of the bottom remote from the open end curves in the shape of a parabola.

Two sides extend longitudinally from the open end in a generally vertical orientation. Preferably, the sides curve continuously from vertical to horizontal orientation and curve transversely generally following the perimeter of the bottom.

Preferably, the front portion extends transversely between the sides in a generally vertical orientation. The front preferably curves continuously upward from vertical to horizontal orientation and curves transversely generally following the parabolic curve of the bottom.

Preferably, a curved joining region connects the bottom to the sides and the front. The joining region preferably curves continuously upward from horizontal to vertical orientation along the perimeter of the bottom adjacent the sides and the front.

Preferably, the top portion extends longitudinally from the open end in a generally horizontal orientation. The top preferably curves continuously downward from horizontal to vertical orientation joining the sides and the front.

Preferably, the bubble also comprises stiffening means and at least one ventilation hole through it. The stiffening means preferably extend longitudinally along the sides in the form of curved ridges protruding from the sides. The ventilation holes are preferably located on the sides and top, allowing air to circulate through the bubble portion of the protection device while it is worn.

To retain the bubble in place on the limb with the limb extremity within the bubble, the device preferably includes first gender hook and loop connector gripping strips and a sinuous elastic gripping strap having a surface that comprises a second gender hook and loop connector. The bubble gripping strips are preferably fixedly attached to the bubble, while the gripping strap is not fixedly attached to the bubble. Instead, at both ends, the gripping strap is adaptable for removable connection with the bubble gripping strips. Preferably, the bubble gripping strap also has a central portion that wraps around the limb to secure the bubble on the limb.

To protect the bubble from wear, a conventional surgical boot removably attaches to the bubble. The boot preferably comprises a sole, an enclosure, at least one boot gripping strap and at least one boot gripping strip. Preferably, the boot gripping strips and the boot gripping straps are removably connectable, preferably comprising first and second gender hook and loop fasteners such as VELCRO. The sole preferably has a generally planar top surface so that the bubble bottom can rest upon the top surface.

Preferably, the enclosure extends substantially vertically and joins the sole along the perimeter of the sole. The boot gripping strips preferably comprise a first gender hook and loop connector and are fixedly attached to the enclosure, positioned in such a way to retain the bubble within the enclosure. The boot gripping straps are preferably made of a second gender hook and loop connector so that they can be removably connected with the boot gripping strips and can also be removably connected with the bubble gripping strips to secure the bubble within the enclosure.

This invention also provides methods for using an orthopedic protection device to protect a limb extremity. According to one method, a limb extremity is placed within a protective enclosure to which hook and loop connector strips are attached. The protective enclosure is secured to the limb by wrapping a sinuous elastic hook and loop strap around the limb, and connecting the strap to the hook and loop strips that are on the protective enclosure.

A further method includes placing the protective enclosure in a surgical boot which has an exterior on which a hook and loop connector strip and sinuous hook and loop connector strap are attached. The protective enclosure is secured within the surgical boot by wrapping the surgical boot hook and loop connector strap around the surgical boot and attaching the surgical boot hook and loop connector straps to the hook and loop connector strips attached to the surgical boot.

DETAILED DESCRIPTION OF THE PREFERRED EMBODIMENTS AND BEST MODE CONTEMPLATED FOR PRACTICING THE INVENTION

Figure 1:
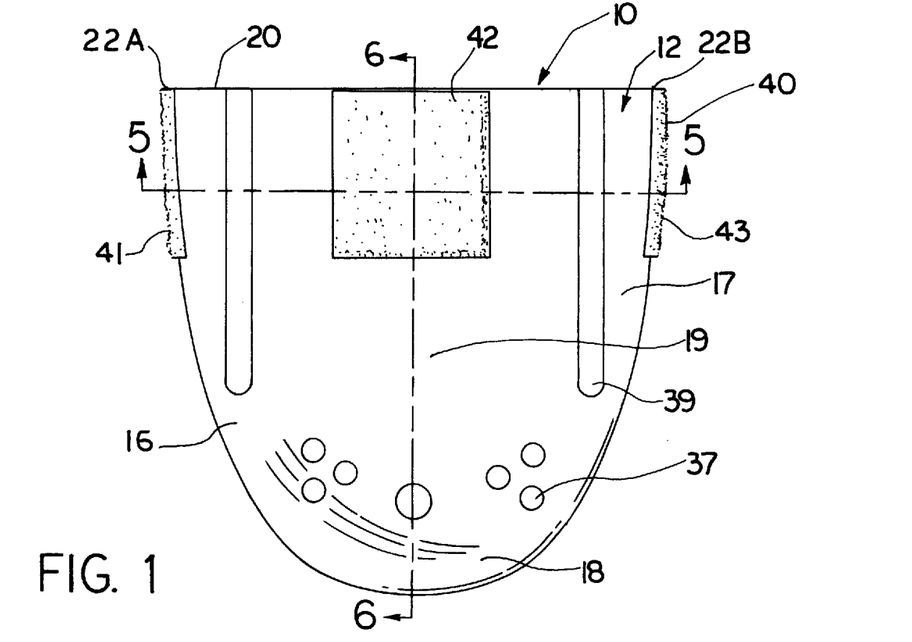
FIG. 1 is a top view of a bubble portion of an orthopedic protection device manifesting aspects of the invention.
Figure 7:
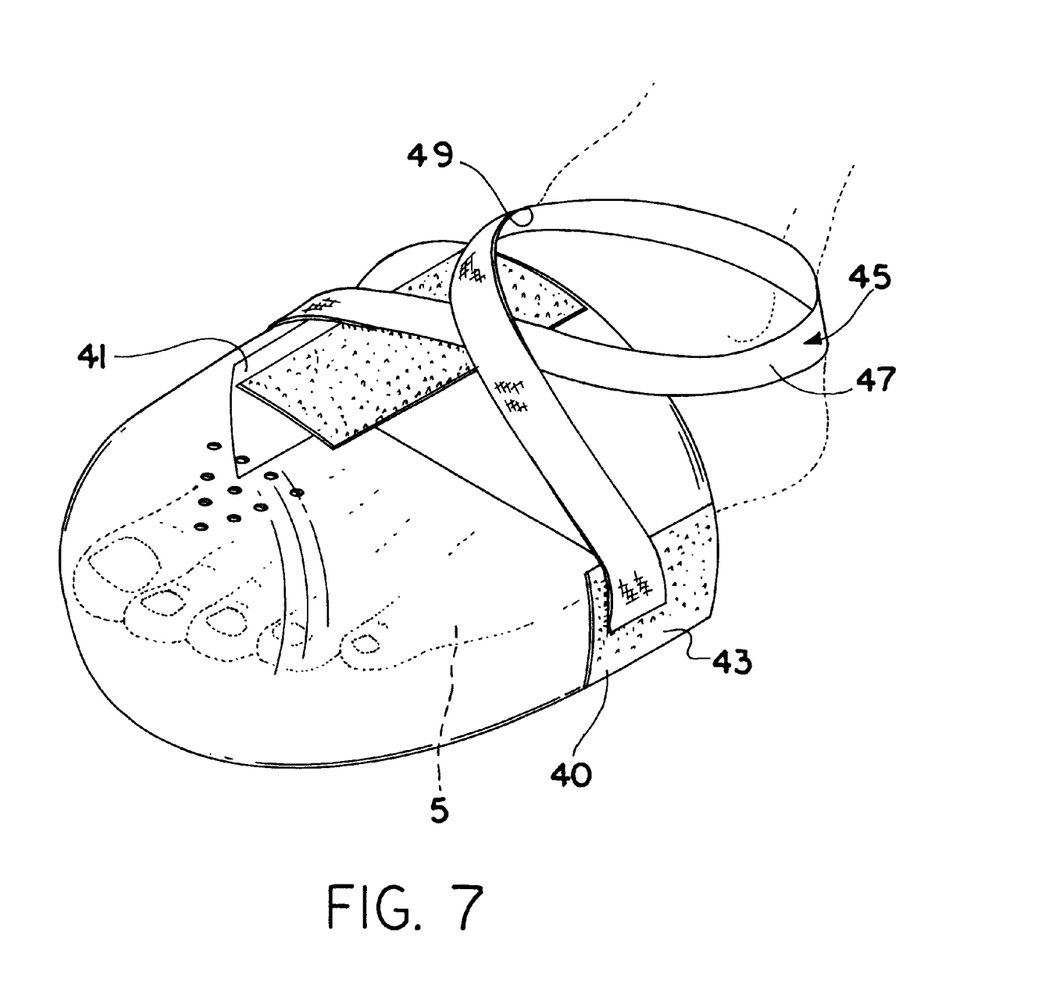
FIG. 7 is an isometric view of the an orthopedic protection device manifesting aspects of the invention, with a foot shown in phantom lines.

Referring now to the drawings in general, and FIGS. 1 and 7 specifically, the preferred embodiment of an orthopedic protection device manifesting aspects of the invention is designated generally 10, and includes a bubble 12, and means for securing bubble 12 to a limb extremity 5 comprising bubble gripping strips 40 and at least one bubble gripping strap 45.

Figure 4:
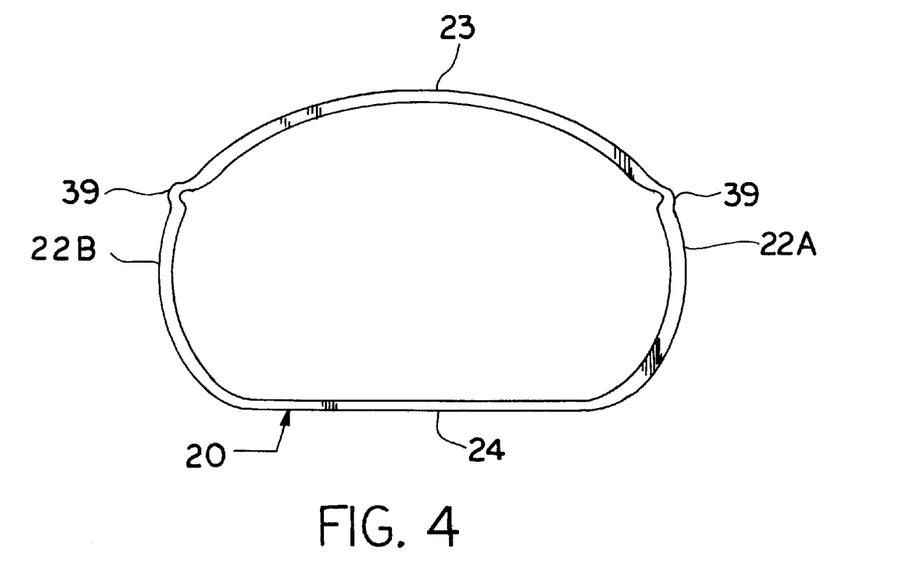
FIG. 4 is a rear elevation view of the bubble portion shown in FIG. 1, with the thickness of the device exaggerated for illustrational purposes.

Bubble 12 has an open end 20 so that a limb extremity 5, such as toes and part of the foot, can be placed into bubble 12 and protected. As illustrated in FIG. 4, the perimeter of open end 20 comprises two substantially vertical edges 22, namely a left edge 22A and a right edge 22B, a substantially horizontal top edge 23, and a substantially horizontal bottom edge 24.

Figure 2:
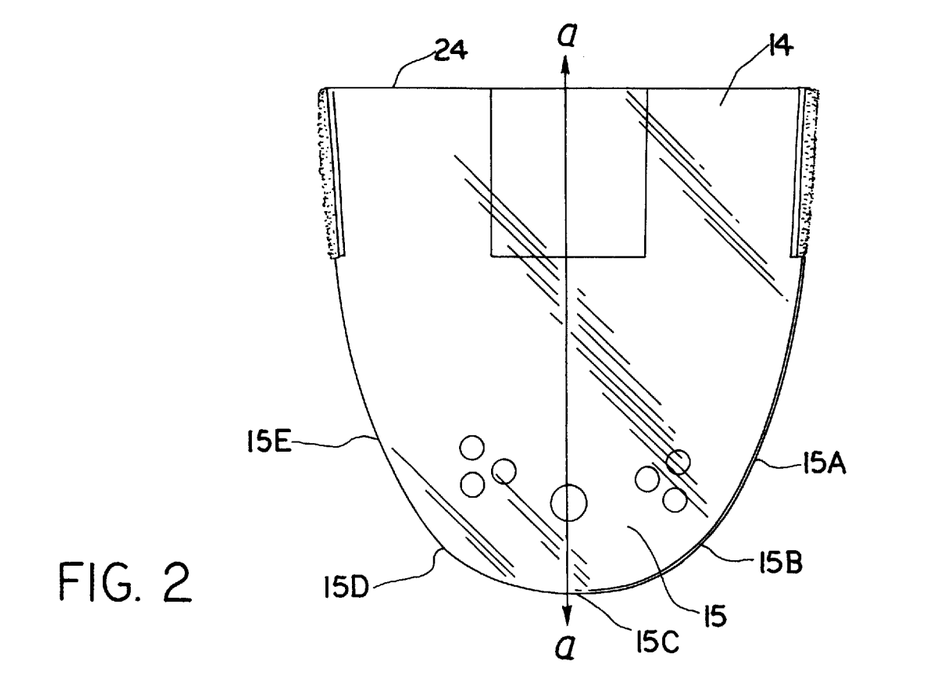
FIG. 2 is a bottom view of the bubble portion shown in FIG. 1.
Figure 3:
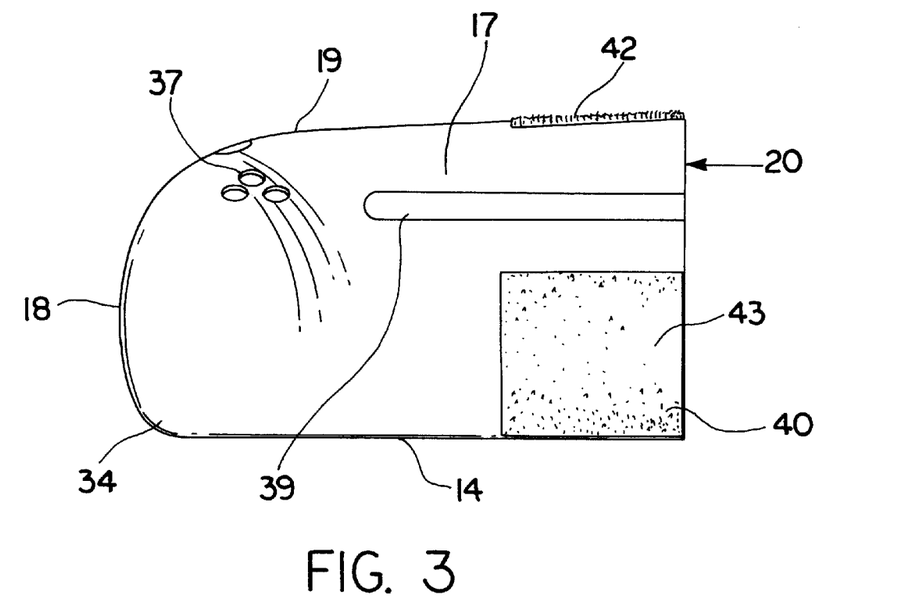
FIG. 3 is a right side elevation view of the bubble portion shown in FIG. 1.

As shown in FIGS. 1 through 3, bubble 12 comprises several portions. A generally planar bottom 14 extends longitudinally from open end bottom 24. Two side portions, left side 16 and right side 17, extend along the perimeter of bottom 14 longitudinally away from vertical edges 22 in a generally vertical orientation. A front portion 18 extends transversely from side portions 16 and 17 following the perimeter of bottom 14, remote from open end 20 in a generally vertical orientation. Extending longitudinally from top edge 23 in a generally horizontal orientation, top portion 19 connects sides 16 and 17 and front 18.

Figure 5:
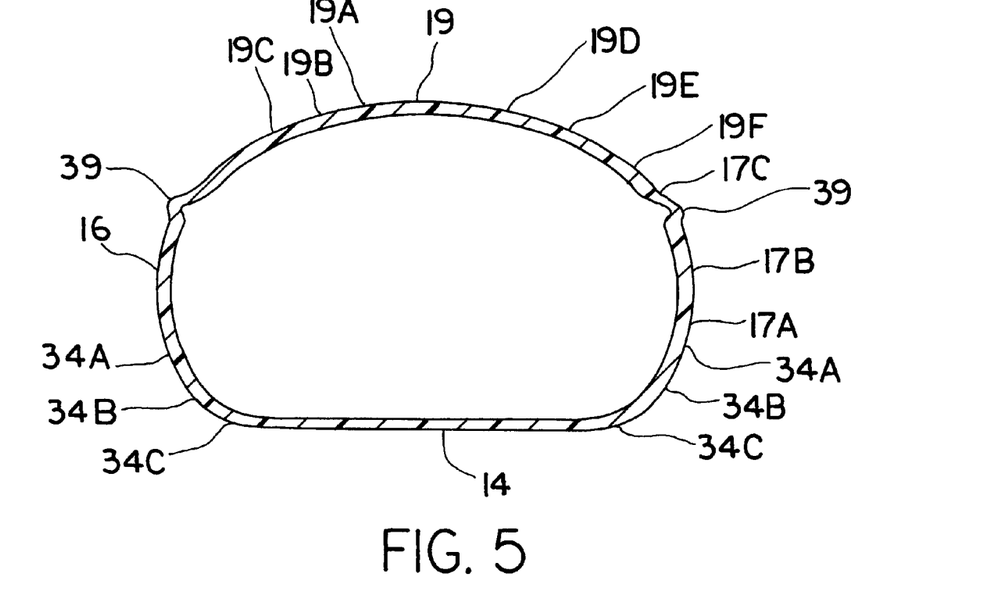
FIG. 5 is a transverse cross sectional view of the bubble portion shown in FIG. 1, taken along line 5—5, with the thickness of the device exaggerated for illustrational purposes.

A bottom joining region 34 connects bottom portion 14 to sides 16 and 17, and to front 18. Bottom joining region 34 extends around the perimeter of bottom 14 adjacent sides 16 and 17, and front 18. As shown in FIG. 5, bottom joining region 34 extends substantially horizontally at point 34C where bottom joining region 34 intersects bottom 14. From the point of intersection with bottom 14, bottom joining region 34 curves continuously upward from horizontal to vertical orientation from 34A to 34B to 34C until bottom joining region 34 extends substantially vertical at the point of intersection with sides 16 and 17.

Bubble 12 can be configured so that it can accommodate the extremity of only a right or a left foot. However, in the preferred embodiment, bubble 12 is symmetric about a vertical plane extending longitudinally from open end 20, so that bubble 12 can accommodate the extremity of either a right or left foot.

In the preferred embodiment, bubble 12 curves to conform closely to the shape of a foot, as detailed in the following description. As illustrated in FIG. 2, the end of bottom 14 remote from open end 20 curves in the shape of a parabola, forming parabolic end 15. Parabolic end 15 curves transversely in a horizontal plane from 15A to 15B to 15C. Parabolic end 15 is symmetric across line a—a, so that the portion curving from 15C to 15D to 15E mirrors the portion curving from 15A to 15B to 15C.

Preferably, sides 16 and 17 also curve to conform to the shape of a foot. Both sides curve continuously from vertical to horizontal orientation until intersecting top 19. As shown in FIG. 5, the rate of curvature of side 17 increases as side 17 approaches top 19. Therefore, from 17A to 17B the rate of curvature of side 17 is less than the rate of curvature from 17B to 17C. Side 17 also curves laterally as it extends away from vertical edge 22B, following the curve of bottom 14. Because bubble 12 is symmetric in the preferred embodiment, side 16 mirrors the curves of side 17.

Figure 6:
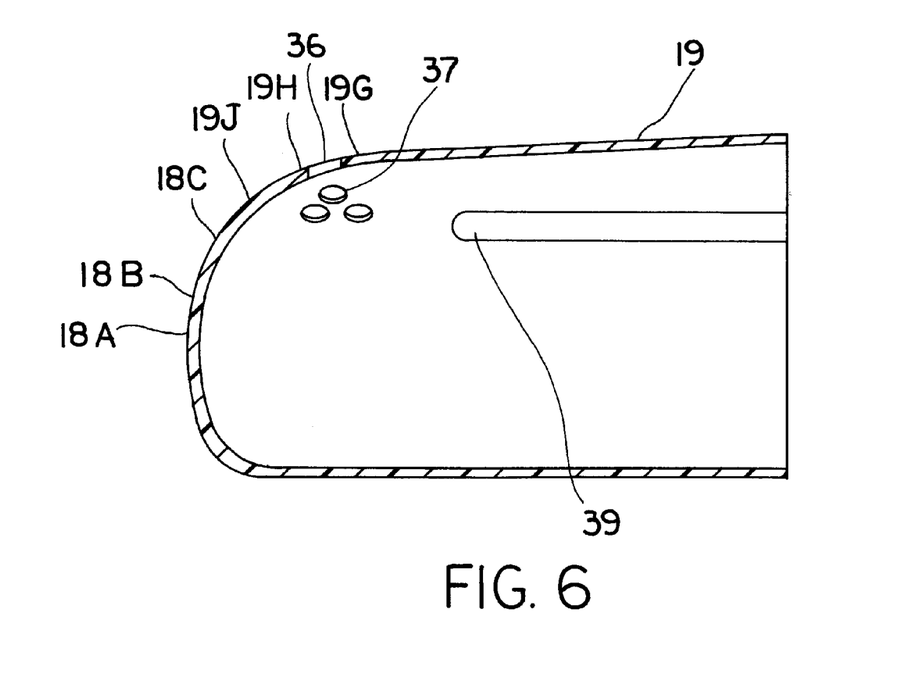
FIG. 6 is a longitudinal cross sectional view of the bubble portion shown in FIG. 1, taken along line 5—5, with the thickness of the device exaggerated for illustrational purposes.

Preferably, top 19 curves continuously downwardly, intersecting sides 16 and 17 and front 18. Top 19 curves continuously downward laterally from 19A to 19B to 19C intersecting side 16 and from 19D to 19E to 19F intersecting side 17. As shown in FIG. 6, top 19 also curves continuously downward longitudinally from 19G to 19H to 19J intersecting front 18.

Preferably, front 18 curves continuously upward from vertical to horizontal orientation in three planes creating a smooth bulbous portion. As shown in FIG. 6, front 18 curves longitudinally upward from vertical to horizontal orientation from 18A to 18B to 18C until intersecting top 19. Front 18 also curves laterally following the parabolic end 15 of bottom 14. Because it continuously curves laterally, longitudinally and vertically, front 18 has no flat areas.

The preferred embodiment also includes a plurality of stiffeners 39. As illustrated in FIGS. 4 and 6, stiffeners 39 extend longitudinally along sides 16 and 17, protruding from the exterior of bubble 12 in the shape of a curved ridges. Although the number of stiffeners 39 can vary, the preferred embodiment includes two.

Because bubble 12 encloses limb extremity 5, it includes at least one ventilation hole 36 to allow air to circulate through bubble 12. Although the size, location and number of ventilation holes 36 can vary, the preferred embodiment has two different size ventilation holes: a three-eighths inch diameter hole; and six one-quarter inch diameter holes. In the preferred embodiment bubble 12 has: a three-eighths inch diameter ventilation hole 36 through top 19 remote from open end 20; three one-quarter inch diameter ventilation holes 37 through left side 16 remote from open end 20; and three one-quarter inch diameter ventilation holes through right side 17 remote from open end 20.

Although bubble 12 can be made from numerous materials, preferably it is a single piece structure made from 0.07 inch thick PVC #87644 plastic. Preferably the plastic is clear to allow visual inspection of the extremity without removing orthopedic protection device 10.

The dimensions of bubble 12 can be altered to fit different sized foot extremities. However, in the preferred embodiments, the length of bubble 12 is approximately twice the height, and the width is approximately 50 percent greater than the height. Specifically, the length from open end 20 to point 15C on parabolic end 15 is approximately 7 inches, the width between left edge 22A and right edge 22B is approximately 4¾ inches, and the height from bottom edge 24 to top edge 23 is approximately 3¼ inches.

As illustrated in FIG. 7, bubble 12 is held in place on the limb by using a plurality of gripping strips 40 connected to bubble 12 and at least one gripping strap 45. The gripping strap 45 comprises a sinuous strap 47 and a gripping surface 49 on at least one surface of sinuous strap 47. Sinuous strap 47 is preferably elastic, and gripping strips 40 and gripping straps 45 preferably are substantially the same width.

One end of each gripping strap can be fixedly attached to bubble 12. In the preferred embodiment, gripping strap 45 comprises a sinuous strap that comprises a gripping surface 49 along its entire length. Having a gripping surface 49 along the entire length of sinuous strap 47 allows gripping strap 45 to be removably connected to gripping strips 40 at both ends.

Gripping strips 40 extend longitudinally along upper portion 16 of bubble 12. Although the number of gripping strips can vary, the preferred embodiments comprise three gripping strips 40 fixedly attached by an adhesive to bubble 12. As shown in FIG. 1, preferably one gripping strip 43 is located on right side 17 adjacent open end 20, one gripping strip 41 is located on left side 16 adjacent open end 20, and one gripping strip 42 is located on top 19 adjacent open end 20. Preferably, side gripping strips 41 and 43 are substantially the same length and top gripping strip 42 is longer than side gripping strips 41 and 43.

For ease of use, gripping strips 40 and gripping straps 45 should be connectable by applying hand pressure. Preferably, gripping strips 40 and gripping strap 45 comprise hook and loop connectors such as VELCRO. Preferably, gripping strips 40 are made of a first gender hook and loop connector strip and gripping strap 45 is made of an sinuous elastic strap having second gender hook and loop connectors on the entire length of one surface as shown in FIG. 7. This allows gripping strips 40 and gripping strap 45 to be connected and disconnected easily and frequently without significant damage to either gripping strips 40 or gripping strap 45.

To hold bubble 12 in place on limb 5, at least one gripping strap 45 wraps around a portion of limb 5 outside bubble 12, and connects to gripping strips 40. As illustrated in FIG. 7, preferably, gripping surface 49 connects to right side gripping strip 43, gripping strap 45 wraps around the limb, and gripping surface 49 connects to left side gripping strip 41.

Figure 9:
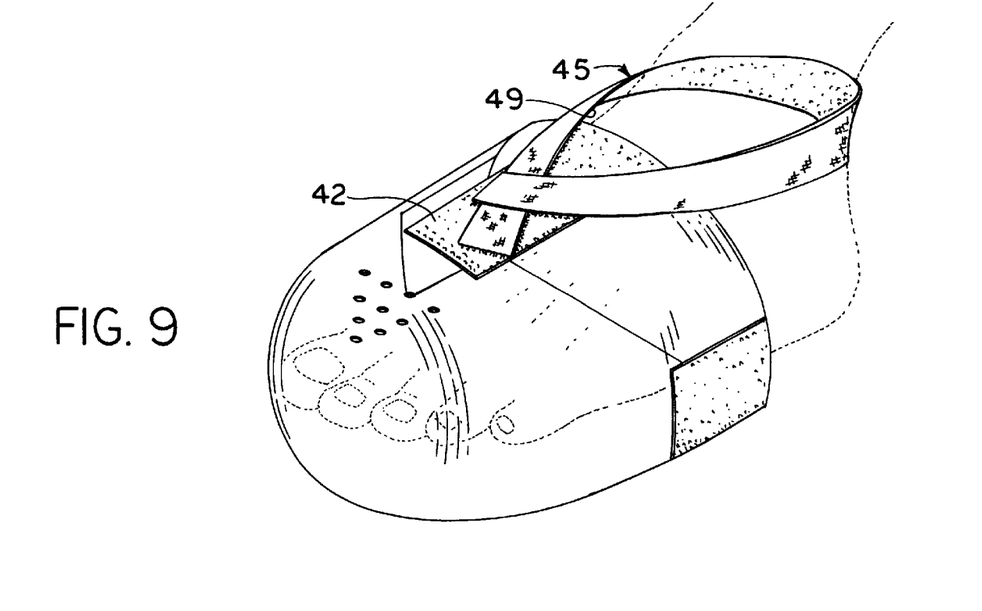
FIG. 9 is an isometric view showing an alternative configuration for securing the device shown in FIG. 7 to a limb, which is shown in phantom lines.

As illustrated in FIG. 9, the previously mentioned connection between side gripping strips 41 and 43, and gripping strap 45 can vary. In FIG. 9, both ends of gripping strap 45 connect to top gripping strip 42 located on top 19. This second connection configuration can be used in place of or in connection with the preferred connection configuration.

Figure 8:
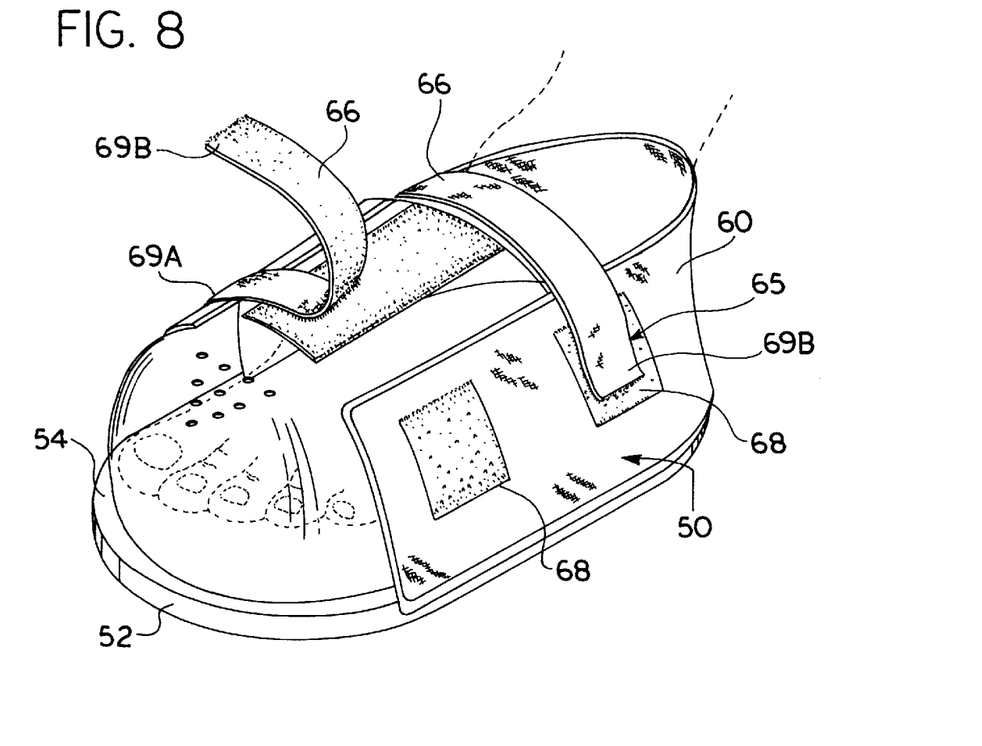
FIG. 8 is an isometric view of the device shown in FIG. 7, used in conjunction with a surgical boot, with a foot shown in phantom lines.

FIG. 8 illustrates a separate embodiment in which orthopedic protection device 10 operates in conjunction with a conventional surgical boot 50. Preferably, surgical boot 50 comprises a sole 52, an enclosure 60 and attachment means 65. Sole 52 is made from a material that protects orthopedic protection device 10 and a cast from deterioration resulting from contact when the patient walks. In the preferred embodiments, sole 52 is made from a rubber material. Preferably, sole 52 has a planar top surface 52 to provide a constant interface between planar bottom 14 of bubble 12 and top surface 54. Enclosure 60 extends substantially vertically and attaches to the perimeter of sole 52. Preferably enclosure 60 is made of a sinuous material such as canvas.

As illustrated in FIG. 8, in the preferred embodiment for the combination of orthopedic protection device 10 and surgical boot 50, attachment means 65 comprises at least one and preferably two sinuous boot gripping straps 66 and at least one and preferably two boot gripping strips 68. Preferably, one end 69A of each boot gripping strap 66 is fixedly attached to enclosure 60 and one end 69B of boot gripping strap 66 is not fixedly attached. Boot gripping strips 68 are preferably fixedly attached to a portion of enclosure 60 remote from where fixed ends 69A are attached to enclosure 60.

Preferably, boot gripping strips 68 and boot gripping straps 66 are made of opposing gender hook and loop fasteners such as VELCRO so they can be connected and disconnected easily and frequently without significant damage to either boot gripping strips 68 or boot gripping straps 66. Additionally, to facilitate connection between surgical boot 50 and orthopedic protection device 10, boot gripping straps 66 are preferably made of hook and loop connectors of the opposite gender of gripping strips 40 attached to bubble 12.

When used in conjunction with surgical boot 50, orthopedic protection device 10 is preferably first secured to limb 5 as previously described and as illustrated in FIG. 7. Bubble 12 is placed on inner surface 54 so that enclosure 60 encloses at least part of bubble 12. As illustrated in FIG. 8, surgical boot 50 is held in place by connecting an intermediate section of boot gripping strap 66 with top gripping strip 42 attached to bubble 12, and then connecting free end 69B to boot gripping strip 68.

While the preferred embodiments of the invention have been described above and alternative embodiments have also been described, the scope of protection to which the invention is believed entitled is defined by the claims and by equivalents thereto which perform substantially the same function in substantially the same way to achieve substantially the same result as set forth in the claims, so long as such substantial equivalents, as defined by a claim for such substantial equivalent, do not read on the prior art.

I claim:

1. An orthopedic protection device for protecting the extremity of a limb comprising:
   a. an open-ended bubble;
   b. gripping means for removably securing said bubble in place on the limb during use of said bubble with the limb extremity within said bubbles,
      wherein said open-ended bubble comprises:
      c. an end having an opening for inserting the limb extremity into said bubble, said opening having a right and a left substantially vertical edge, a substantially horizontal top edge and a substantially horizontal bottom edge;
d. a longitudinally elongated, generally planar bottom portion extending from said bottom edge;
e. two longitudinally elongated sides extending from said right and left vertical edges in a generally vertical orientation and connected to said bottom portion;
f. a front portion extending transversely from said sides in a generally vertical orientation connecting said sides and connected to said bottom portion;
g. a longitudinally elongated top portion extending from said top edge in a generally horizontal orientation and connected to said front portion and said sides;
wherein said gripping means comprise:
h. bubble gripping strip means connected to said bubble;
i. sinuous bubble gripping strap means for removably connecting with said bubble gripping strip means,
said bubble gripping strip means being positioned to retain said bubble in place on the limb extremity when in use, and connecting to a surgical boot to retain said bubble within said surgical boot;
wherein said surgical boot comprises:
j. a sole with a generally planar top surface;
k. an enclosure extending substantially vertically and joining said sole along the perimeter of said sole;
l. means for securing said bubble in place within said surgical boot, comprising:
i. boot gripping strap means connected to said enclosure, and
for removably connecting with said bubble gripping strip means to secure said bubble within said surgical boot.

2. The protection device of claim 1 wherein said bubble gripping strip means comprise a first gender hook and loop connector and said boot gripping strap means comprise a second gender hook and loop connector.

3. The protection device of claim 2 wherein said bubble gripping strip means are substantially the same length.

4. The protection device of claim 3 wherein one bubble gripping strip means extends longitudinally adjacent said open end along said top portion.

5. The protection device of claim 4 further comprising a plurality of said bubble gripping strip means of substantially the same width.

6. An orthopedic protection device for a limb extremity comprising:
a. an open-ended bubble comprising:
i. an end having an opening for inserting the limb extremity into said bubble, said opening end having two substantially vertical edges, a substantially horizontal top edge and a substantially horizontal bottom edge;
ii. a longitudinally elongated, generally planar bottom portion extending from said bottom edge with an end remote from said opening end curving in the shape of a parabola;
iii. two longitudinally elongated sides extending from said vertical edges in a generally vertical orientation, curving continuously from vertical to horizontal orientation and curving transversely generally following the perimeter of said bottom portion;
iv. a front portion extending transversely from said sides in a generally vertical orientation connecting said sides, curving continuously upward from vertical to horizontal orientation and curving laterally generally following the perimeter of said bottom portion remote from said opening;
v. a joining region connecting said bottom portion to said sides and said front portion curving continuously upward from horizontal to vertical orientation along the perimeter of said bottom portion adjacent said sides and said front portion;
vi. a longitudinally elongated top portion extending from said top edge in a generally horizontal orientation, curving continuously downward from horizontal to vertical orientation joining said sides and said front portion; and
b. gripping means for securing said bubble in place on the limb extremity when said bubble is in use with the limb extremity within said bubble,
wherein said bubble further comprises stiffening means; wherein said stiffening means extend longitudinally along said sides;
wherein said stiffening means are curved ridges protruding from said sides, wherein said bubble is transparent.

7. The protection device of claim 6 wherein said bubble is one piece.

8. The protection device of claim 7 wherein said bubble is made from plastic.

9. The protection device of claim 8 wherein said bubble has at least one ventilation hole.

10. The protection device of claim 9 wherein said bubble has at least two ventilation holes and at least one of said ventilation holes is through one of said sides.

11. The protection device of claim 10 wherein the length from said open end is approximately twice the height from said top portion to said bottom portion.

12. The protection device of claim 11 wherein the width from left edge to right edge is approximately fifty percent greater than said height.

13. The protection device of claim 12 wherein said length is approximately seven inches.

14. The protection device of claim 13 wherein said height is approximately three and a quarter inches.

15. The protection device of claim 14 wherein said width is approximately four and three-quarters inches.

16. An orthopedic protection device for a limb extremity comprising:
a. an open-ended bubble;
b. a surgical boot connected to said bubble;
c. gripping means for securing said bubble in place on the limb extremity when said bubble is in use with the limb extremity within said bubble;
wherein said open-ended bubble comprises:
i. an end having an opening for inserting the limb extremity into said bubble interior, said opening having two substantially vertical edges, a substantially horizontal top edge and a substantially horizontal bottom edge;
ii. a longitudinally elongated, generally planar bottom portion extending from said bottom edge;
iii. two longitudinally elongated sides extending from said vertical edges in a generally vertical orientation and connected to said bottom portion;
iv. a front portion extending transversely from said sides in a generally vertical orientation connecting said sides and said bottom portion; and v. a longitudinally elongated top portion extending from said top edge in a generally horizontal orientation and connected to said sides and said front portion;

wherein said gripping means comprise:
- d. bubble gripping strip means connected to said bubble;
- e. sinuous bubble gripping strap means for removably connecting with said bubble gripping strip means;

wherein said surgical boot comprises:
- f. a sole with a generally planar top surface;
- g. an enclosure extending substantially vertically and joining said sole along the perimeter of said sole;
- h. means for securing said bubble in place within said surgical boot, comprising:
  - i. boot gripping strip means connected to said enclosure and having a gripping means for removably retaining said bubble within said surgical boot by said bubble gripping strip means.

17. An orthopedic protection device for a limb extremity removably connectable with a cast on the limb, comprising:
   a. a transparent, plastic, single-piece, open-ended bubble having at least one ventilation hole formed therein and comprising:
      i. an end having an opening for inserting the limb extremity into said bubble, said opening having two substantially vertical edges, a substantially horizontal top edge and a substantially horizontal bottom edge;
      ii. a longitudinally elongated, generally planar bottom portion extending from said bottom edge, with an end remote from said opening curving in the shape of a parabola;
      iii. two longitudinally elongated sides extending from said vertical edges in a generally vertical orientation, curving continuously from vertical to horizontal orientation and curving transversely generally following the perimeter of said bottom portion;
      iv. a front portion extending transversely from said sides in a generally vertical orientation connecting said sides, curving continuously upward from vertical to horizontal orientation and curving transversely, generally following the perimeter of said bottom portion remote from said opening;
      v. a joining region connecting said bottom portion to said sides and said front portion, curving continuously upward from horizontal to vertical orientation along the perimeter of said bottom portion adjacent said sides and said front portion;
      vi. a longitudinally elongated top portion extending from said top edge in a generally horizontal orientation, curving continuously downward from horizontal to vertical orientation joining said sides and said front portion;
      vii. stiffening means in the form of curved ridges protruding from said sides, extending longitudinally along said sides;
   b. bubble gripping strips comprising a first gender hook and loop connector, fixedly attached to said bubble, and positioned to retain said bubble in place on the limb extremity during use of said bubble with the limb extremity within said bubble;
   c. a sinuous elastic bubble gripping strap comprising a second gender hook and loop connector removably connected to said bubble gripping strips, having a central portion that wraps around the limb to secure said bubble in place on the limb during use of said bubble with the limb extremity within said bubble; and
   d. a surgical boot attached to said bubble comprising:
      i. a sole with a generally planar top surface;
      ii. an enclosure extending substantially vertically and joining said sole along the perimeter of said sole;
      iii. a boot gripping strip comprising first gender hook and loop connector, fixedly attached to said enclosure and positioned to retain said bubble within said enclosure;
      iv. a sinuous boot gripping strap comprising second gender hook and loop connector removably connected to said boot gripping strips and adaptable for connection with said bubble gripping strips to secure said bubble within said enclosure.

* * * * *